United States Patent
Raczek et al.

(10) Patent No.: US 6,911,473 B2
(45) Date of Patent: Jun. 28, 2005

(54) DETECTABLE AGENT FOR WOOD TREATMENT AND METHOD FOR ITS DETECTION

(75) Inventors: Nico N. Raczek, Kelkheim (DE); Ariane Wetzel, Frankfurt am Main (DE)

(73) Assignee: Nutrinova Nutrition Specialties & Food Ingredients GmbH, Frankfurt am Main (DE)

( * ) Notice: Subject to any disclaimer, the term of this patent is extended or adjusted under 35 U.S.C. 154(b) by 32 days.

(21) Appl. No.: 10/305,848

(22) Filed: Nov. 27, 2002

(65) Prior Publication Data

US 2003/0232885 A1 Dec. 18, 2003

(30) Foreign Application Priority Data

Jun. 13, 2002 (DE) .................................... 202 09 157 U

(51) Int. Cl.[7] .................. A01N 37/00; A01N 37/02; A01N 37/04; A01N 37/06; B27K 3/50
(52) U.S. Cl. .................. 514/557; 514/553; 514/554; 514/556; 514/558; 514/559; 514/560; 514/568; 514/569; 514/570; 514/571; 514/572; 514/573; 514/574; 514/575; 514/576; 514/577; 514/578; 514/970; 514/972; 514/974; 424/DIG. 11; 428/541; 252/301.16
(58) Field of Search .................. 514/553, 554, 514/556–560, 568–578, 970, 972, 974; 424/DIG. 11; 428/541; 252/301.16

(56) References Cited

U.S. PATENT DOCUMENTS

| 4,041,176 A | 8/1977 | Metzner et al. ............. 424/318 |
| 4,585,795 A | 4/1986 | Linderborg |
| 4,750,934 A * | 6/1988 | Metzner et al. ............... 106/18 |
| 2001/0018454 A1 * | 8/2001 | Wetzel ....................... 514/557 |

FOREIGN PATENT DOCUMENTS

| DE | 10 80 327 B | 4/1960 | |
| DE | 2 249 202 | 4/1974 | .......... G01N/23/22 |
| DE | 100 03 170 | 2/1997 | .......... A23L/1/308 |
| DE | 297 01 633 U1 | 7/1997 | .......... A01N/37/06 |
| DE | 196 11 868 A1 | 10/1997 | .......... B27K/5/02 |
| DE | 197 03 552 A1 | 8/1998 | .......... A01N/37/06 |
| EP | 0 950 700 A1 | 10/1999 | .......... C09K/3/18 |
| GB | 2 219 810 A | 12/1989 | .......... D06M/11/04 |
| GB | 2268403 * | 1/1994 | |
| GB | 2 301 122 A | 11/1996 | .......... D06M/11/79 |
| JP | 100 67 607 | 3/1998 | |
| WO | WO96/11572 A1 | 4/1996 | .......... A01N/37/02 |
| WO | WO02/17717 A1 | 3/2002 | .......... A01N/43/90 |

OTHER PUBLICATIONS

Chemical Abstracts 113:54235 (1990).*

* cited by examiner

*Primary Examiner*—John Pak
(74) *Attorney, Agent, or Firm*—ProPat, L.L.C.

(57) ABSTRACT

The present invention relates to a composition comprising an organic preservative acid and a UV-active indicator substance for preserving wood and for detection of the sufficient preservation of wood.

12 Claims, No Drawings

DETECTABLE AGENT FOR WOOD TREATMENT AND METHOD FOR ITS DETECTION

The present invention relates to a detectable agent for wood treatment and a method by which the presence of the agent in the wood can be detected.

BACKGROUND OF THE INVENTION

Wood as a material of natural origin, as with all organic materials, is subject to microbiologically caused decay. In addition to *Basidiomycetes*, molds, yeasts and, in rare cases bacteria also, contribute to this decay. Particularly in a moist environment, wood is susceptible to said decay-causing organisms.

The decay-causing organisms also include various wood-staining fungi, which can grow relatively rapidly on wood surfaces which are freshly cut and/or exposed to weathering. This also relates to wood which must be stored under unfavorable conditions, for example in the forest after felling, or under tarpaulins after processing, in particular during transport. The staining, which can be caused, for example, by *Aureobasidium pullulans* is frequent on untreated wood. It is known under the name "blue stain". The presence of such fungi can lead not only to impairment of the appearance of wood or articles produced therefrom, but there is also the hazard that fungi or toxins formed by these can transfer from the wood to other products and that even long-lasting forms of the molds can be given off into the surrounding air. Inspiring such fungi can, in the case of sensitized people, lead to asthma attacks, for example. In addition, the wood is also adversely affected in value, so that infected wood has only a low value or must be destroyed.

For reasons simply of product and consumer protection, a protective treatment is virtually inescapable.

In the timber industry, various wood preservatives are used. Frequently, the constituents of these wood preservatives are substances which are associated with considerable health risk. For example: fluorine compounds (such as copper hexafluoro-silicate, potassium hydrogen fluoride, ammonium hydrogen fluoride), arsenic compounds (principally arsenic pentoxide), boron compounds (such as boric acid, polyboron), copper compounds (for example copper sulfate), tin compounds etc. The chromium compounds which are also used (such as potassium chromate, ammonium dichromate), are no longer biocides in the real sense, since these serve for fixing the biocides in the timber.

The majority of these substances, in accordance with the German dangerous substances ordinance, are toxic or at least hazardous to health. In addition to the odor nuisance due to intensely odorous wood preservatives such as wood tar oils, which is still to be classified as harmless, considerable harm to health can occur merely by contact with some of the abovementioned wood preservatives or correspondingly treated wood.

Despite the required occupational safety measures when such wood treatment agents are used in the industrial sector, the user of wood thus treated frequently is not informed about the possible health risks of direct contact with wood thus treated. In the event of long-lasting direct contact with this wood, the risk of delayed harm to health cannot be excluded.

In addition to the use of such materials in the industrial sector, therefore, use by craftsmen in the house and home sectors is particularly a problem.

Particularly strict measures must be applied to wood which can come into contact with foods, food ingredients, food-contact articles, animal feeds, pet food, cosmetics, food wastes or articles of daily use in the broadest sense. In this case there is always the possibility of direct transfer to these articles, for example foods. Such a transfer must always be avoided in the case of materials which are not suitable for consumption or are even toxic, in order to exclude health risks. However, because it is known that unintentional or indirect contamination cannot be absolutely excluded, it is an object of the invention to achieve sufficient protection of the wood from mold attack, without risks to health resulting from contact with the wood or transfer of the wood preservative to other products such as foods.

Preservatives which are used to preserve various foods have occasionally also been tested for their applicability to preserving wood, in particular in the form of derivatives which are not used as such for food preservation. Some inventions take on this problem and use various acids, some in combination with other substances, for treating wood. Thus, DE-A 100 03 170 (=EP-A 1 123 787) uses sorbic acid and its salts for protecting wood from mold attack. DE-A 197 03 552 describes mold-inhibiting aqueous preparations for indoor applications; here also sorbic acid and its salts are used. U.S. Pat. No. 4,585,795 discloses the use of mixtures of alkali metal salts of organic acids in combination with selected quaternary ammonium salts for protecting wood from mold attack. JP-A 100 67 607 describes a wood insecticide which contains, as active ingredient, at least one $C_6$–$C_{12}$ fatty acid in amounts between 0.01 and 9% by weight. WO-A 96/11572 describes compositions of carboxylic acids having up to 10 carbon atoms and their salts and $C_3$–$C_{10}$ diols or esters of these compounds for cleaning, disinfection, surface treatment, impregnation or antimicrobial treatment.

If wood is treated, for example with solutions of the abovementioned substances, after drying the solution, the previous treatment in most cases is no longer readily detectable. However, for a quality assessment, for further processing and commerce, it is of critical economic importance. Although a treatment can be detected by testing an individual product, this is accompanied by complex chemical analysis and processing. For this the appropriate preservative must, in a complex procedure, be isolated from the wood (for example by extraction with organic solvents), concentrated, identified and quantitated. The results obtained can only be related to the product examined. Large amounts of machined wood or wood in assembled products (for example pallets) in the industrial sector or hand craft sector (such as unworked furniture timber) or the home worker sector may not be examined as a whole. In addition, when the abovementioned methods are used in wood-processing factories, because of the high throughput rates frequently it is not possible to test whether the worked wood has been sufficiently treated at all points, quite apart from the fact that apparatuses for carrying out such testing are expensive and the tests themselves can generally only be carried out by qualified specialists. Such an expenditure is not justified in most cases.

It has already been proposed to add an indicator to the solutions of organic acids or their salts used for wood treatment. Such indicators are prescribed, for example, in DE-A 196 11 868 as a marking agent for timber. However, for this purpose chemical reactions are always used (intensely colored azo dyes are formed in DE-A 196 11 868). Not only the substances used but also the chemicals required for the coupling are generally of toxicological concern. Furthermore, only point tests can be performed using this method and lead to staining at the points of study.

WO-A 02/17717 describes a fluorescent agent which indicates whether water intended for use with flowers has been adequately supplied with appropriate treatment agents for cut flowers.

EP-A 0 950 700 describes the use of optical brighteners in aircraft de-icing compositions for improving the detection of the use of de-icing compositions.

There is still a requirement for a simple, inexpensive and rapidly performed test which gives information as to whether wood has been appropriately treated or not.

BRIEF DESCRIPTIONS OF THE INVENTION

The present invention now makes available a detectable agent for wood treatment and a method by which the presence of the agent in wood can be detected. The inventive agent comprises a preservative acid and a UV-active indicator substance.

DETAILED DESCRIPTION OF THE INVENTION

A wood treated with this agent can then be irradiated using a simple UV lamp, fluorescence occurring indicating the presence of the wood preservative.

The present invention uses an optical converter which converts the incident ultraviolet radiation (180–400 nm) into longer-wave light and leads to the appearance of fluorescence. By this means not only are all wood parts to be tested for treatment in a very short run time, but also subsequent industrial branches can check the treatment. Agents are used in this method which are either already used as additive, for example in foods or food-contact articles, or have had a very favorable toxicological rating (for example: GRAS "generally recognized as safe" in the USA) in products of daily use. Expediently, the UV-active indicator substances should be water-soluble so that they can be applied evenly in aqueous solution to the wood to be treated, for example by sprinkling, spraying, dipping or impregnation.

Preservatives, in the context of the invention, are in particular organic preservative acids, for example formic acid, acetic acid, propionic acid, lactic acid, sorbic acid, benzoic acid and mixtures of the same. Also coming under this term are the alkaline earth metal salts and alkali metal salts of these acids and mixtures of the same. In addition, this term is also to be taken to mean mixtures of acid(s) and salt(s) of different acids.

Suitable UV-active indicator substances for the purposes of the present invention are in principle all such compounds which convert UV light into visible light. However, many of these UV-active substances, owing to their chemical composition, exhibit unwanted reactions with highly concentrated acid solutions or solutions of the salts. In the acid solutions, hydrolytic cleavage of the added UV-active substances frequently occurs. In the salt solutions, flocculation, strong discolorations or even polymerization reactions occur after a relatively long storage time (approximately 3 months) in daylight. Preferred UV-active indicator substances are therefore those which do not exhibit the above described reactions. Suitable substances for combining with the preservative solutions are particularly the following water-soluble UV-active indicator substances, alone or in mixtures: derivatives of flavonic acid (4,4'-diamino-2,2'-stilbenedisulfonic acid), 4,4'-distyrylbiphenylene, methylumbelliferone, coumarin, dihydroquinolinone, 1,3-diarylpyrazoline, naphthalimide, benzoxazole, benzisoxazole and benzimidazole systems linked via CH=CH bonds (for example 5,7-dimethyl-2-(4'-phenylstilbene-4-yl) benzoxazole or salts of 2,5-di(1-methylbenzimidazol-2-yl) furan) and heterocycle-substituted pyrene derivatives and combinations of said UV-active indicator substances. Particular preference is given to naturally occurring purine derivatives, such as caffeine, theophylline or xanthine or combinations of these substances. Furthermore, preferably, substances which are harmless to health are to be used, such as riboflavin, quinine, chlorogenic acid or quinoline yellow or combinations of these compounds.

The combination of the preservative acids with the above named preferred UV-active indicator substances surprisingly does not show any disadvantageous reactions, but the combinations are instead stable, even at room temperature over a storage period of 6 months with simultaneous solar irradiation. Surprisingly, quenching of fluorescence does not occur either, but the UV activity can readily be detected by irradiation with UV light not only on the wood while it is still moist, but also after drying. Furthermore, the treated timbers, after addition of the UV-active indicator substances surprisingly exhibit a further prolonged keeping quality compared with treatment with the pure preservative acid solutions.

The inventive agents comprising preservative acid and UV-active indicator substance can also be spray-dried to form granules or powder, which can then be used dissolved in water.

If these granules are dissolved in water or final solutions are prepared from the abovementioned substances as a mixture, for improved handling and miscibility in a continuous process, thickeners can also be added at a small percentage, for example: mono- and diglycerides of edible fatty acids, starch, agar, alginates (for example sodium or potassium alginate), carrageenan, guar meal, tragacanth, xanthan, cellulose and derivatives thereof (for example methylcellulose, hydroxypropylcellulose, carboxymethylcellulose (CMC)), pectin, gum arabic, gelatin, albumins, caseinates, polyols such as hexylene glycol, butylene glycol, propylene glycol, propane-1,2-diol, 2-methyl-2,4-pentanediol, heptanediol, octanediol, nonanediol, decanediol.

In addition, if appropriate, antifoaming agents (antifoams) can be added, which decrease any foam formation which occurs. Antifoams can be, for example, polyethylene/propylene glycol ether, alkyl polyethylene glycol ether, long-chain alcohols such as isooctanol or silicone-based compositions (for example TEGO Antifoam®, from Goldschmidt-Degussa).

The content of preservative acids in the aqueous stock solution in this case is between 15.0 and 55.0% by weight, preferably between 17.5 and 52.5% by weight, particularly preferably between 20.0 and 50.0% by weight. The content of UV-active indicator substance in the aqueous stock solution is between 0.001% by weight and 5% by weight, preferably between 0.01% and 2.5% by weight. Thickeners can be added to the stock solution if appropriate up to 10% by weight. Antifoams are added if appropriate at concentrations up to 0.15%. The abovementioned spray-dried powders or granules can be prepared from the stock solutions thus composed. For use, these solutions are diluted with water at ratios >1 (volume fraction of stock solution).

The invention is described in more detail below on the basis of examples.

EXAMPLE 1

0.20% by weight of Hostalux® N2R 200, liquid (cationic pyrazoline derivative, Clariant, Muttenz, Switzerland) is added to a 15% strength by weight sodium benzoate solution and the resultant solution is mixed thoroughly with 4 parts by volume of water in a dipping bath. The resultant solution is used for dipping freshly cut planks from freshly felled spruce trees.

EXAMPLE 2

0.05% by weight of Leukophor® U liquid (anionic stilbene derivative, Clariant, Muttenz, Switzerland) is added to a 20% strength by weight calcium propionate solution. This solution is mixed with 4 parts by volume of water and sprayed by means of mobile sprays onto freshly felled debarked pine trunks before storage or transport.

EXAMPLE 3

0.15% by weight of Hostalux® N2R 200, liquid (cationic pyrazoline derivative, Clariant, Muttenz, Switzerland) and 2.0% by weight of caffeine are added to a 55% strength by weight potassium sorbate solution and the solution is mixed thoroughly. This solution is diluted in a continuous process with 9 parts by volume of water and used immediately for sprinkling freshly cut planks from freshly felled pine trees.

EXAMPLE 4

0.25% by weight of Leukophor® U liquid (anionic stilbene derivative, Clariant, Muttenz, Switzerland) is added to a 15% strength by weight sodium benzoate solution. The resultant solution is diluted with 19 parts by volume of water and used for sprinkling freshly cut planks from freshly felled pine trees.

EXAMPLE 5

0.175% by weight of Leukophor® U liquid (anionic stilbene derivative, Clariant, Muttenz, Switzerland) is added to a 15% strength by weight sodium benzoate solution and mixed with 1.0% by weight of quinine hydrochloride dihydrate. This suspension is diluted with 9 parts by volume of water with stirring in a reservoir tank and continuously sprayed onto freshly cut spruce planks.

EXAMPLE 6

0.15% by weight of Hostalux® N2R 200, liquid (cationic pyrazoline derivative, Clariant International Ltd.), 2% by weight of caffeine and 7.5% by weight of propane-1,2-diol are mixed in a 50% strength by weight potassium sorbate solution. The solution is mixed continuously with 19 parts by volume of water and sprayed onto freshly sawn wooden planks.

EXAMPLE 7

0.15% by weight of Hostalux® N2R 200, liquid (cationic pyrazoline derivative, Clariant International Ltd.), 2% by weight of caffeine and 7.5% by weight of 2-methyl-2,4-pentanediol are mixed in a 50% strength by weight potassium sorbate solution. The solution is mixed continuously with 19 parts by volume of water and sprayed onto freshly sawn wooden planks.

EXAMPLE 8

0.25% by weight of Leukophor® U liquid (anionic stilbene derivative, Clariant, Muttenz, Switzerland) is dissolved in a 40% strength by weight potassium sorbate solution and 2.0% by weight of caffeine and 2.5% by weight of carboxymethylcellulose are added. This solution is continuously diluted with 19 parts by volume of water and used for treating freshly sawn wooden planks.

EXAMPLE 9

0.25% by weight of Hostalux® N2R 200, liquid (cationic pyrazoline derivative, Clariant International Ltd.) is added to a 20% strength by weight calcium propionate solution. After intense stirring, 5.0% by weight of propane-1,2-diol are added. This solution is continuously mixed with 6 parts by volume of water and sprayed constantly onto freshly sawn wooden planks.

EXAMPLE 10

0.15% by weight of Hostalux® N2R 200, liquid (cationic pyrazoline derivative, Clariant International Ltd.), 2% by weight of caffeine and 7.5% by weight of 1,2-propanediol are dissolved in a 50% strength by weight potassium sorbate solution. This solution is dried in a vacuum belt drier. A slightly brownish flaky coarse powder is obtained. The powder can be used directly in the solution for wood treatment. For this, 4.5% by weight of the powder are dissolved in mains water and freshly sawn wooden planks are dipped therein.

EXAMPLE 11

0.3% by weight of Leukophor® U liquid (anionic stilbene derivative, Clariant, Muttenz, Switzerland) is dissolved in a 45% strength by weight potassium sorbate solution and 2% by weight of caffeine and 7.5% by weight of 2-methyl-2,4-pentanediol are added thereto. The resultant solution is gently evaporated in vacuo at approximately 60° C. to approximately 15–10% by weight dry matter and then spray-dried. From this powder, 5% strength by weight solutions are prepared for sprinkling freshly sawn wooden planks.

EXAMPLE 12

0.25% Leukophor® liquid (anionic stilbene derivative, Clariant, Muttenz, Switzerland) is dissolved in a 50% strength by weight potassium sorbate solution and 0.05% by weight S 670® (polymethyl/dimethylsiloxane, Wacker, Munich, Germany) is added. This solution is continuously diluted with 19 parts by volume of water and used for treating freshly sawn wooden planks.

EXAMPLE 13

0.175% by weight of Hostalux® N2R 200 liquid (cationic pyrozaline derivative, Clariant, Muttenz, Switzerland) and 0.1% by weight of S 670® (polymethyl/dimethylsiloxane, Wacker, Munich, Germany) are added to a 55% strength by weight potassium sorbate solution and the solution is mixed thoroughly. This solution is diluted in a continuous process with 9 parts by volume of water and immediately used for sprinkling freshly cut planks of freshly felled pine trees.

When the timbers thus treated are irradiated with a UV lamp, for example of wavelength 366 nm, after the treatment solution has dried or else after a longer storage period, they shine intensely white-yellowish, white-violet or white-brownish, depending on the composition of the treatment solution. On the basis of this shining behavior, not only untreated points can be rapidly detected and if necessary retreated, but also the fundamental treatment of the entire plank stack/workpiece can be detected.

What is claimed is:

1. A detectable wood preservative comprising an organic preservative acid or a salt thereof or an organic preservative acid and a salt thereof or mixtures therefrom and a UV-active indicator substance, wherein the organic preservative acid is formic acid, acetic acid, propionic acid, lactic acid, sorbic acid or benzoic acid.

2. A detectable wood preservative as claimed in claim 1, wherein the salt is an alkali metal salt or alkaline earth metal salt.

3. A detectable wood preservative as claimed in claim 1, wherein the UV-active indicator substance is selected from the group consisting of: derivatives of 4,4'-distyrylbiphenylene, stilbenes, flavonic acid, pyrazolines, umbelliferone, coumarin, dihydroquinolinone, naphthalimides, benzoxazole systems, benzisoxazole systems and benzimidazole systems, purine derivatives and heterocycle-substituted pyrene derivatives, riboflavin, quinine, chlorogenic acid, quinoline yellow and combinations thereof.

4. A detectable wood preservative as claimed in claim 3, wherein the UV-active indicator substance is water soluble.

5. A detectable wood preservative as claimed in claim 1, wherein it contains a thickener which is selected from the group consisting of: mono- and diglycerides of edible fatty acids, starch, agar, alginates, carrageenan, guar meal, tragacanth, xanthan, cellulose and its derivatives, pectin, gum arabic, gelatin, albumins, caseinates, polyols and mixtures thereof.

6. A detectable wood preservative as claimed in claim 1, wherein it further comprises an antifoam which is selected from the group consisting of: polyethylene/propylene glycol ether, alkyl polyethylene glycol ethers, long-chain alcohols, polymethyl/dimethylsiloxanes and other silicone-based antifoams.

7. A solution comprising the detectable wood preservative as claimed in claim 1 and water.

8. A wood having a content of the detectable wood preservative as claimed in claim 1.

9. A method for preparing the detectable wood preservative as claimed in claim 1, which comprises mixing an organic preservative acid and a UV-active indicator substance with one another.

10. A method for detecting preserved wood, which comprises adding a UV-active indicator substance to a wood preservative, preserving the wood with this mixture and detecting the presence of the UV-active indicator substance using a UV radiation source, wherein said wood preservative comprises an organic preservative acid and/or a salt thereof.

11. A detectable wood preservative comprising a UV-active indicator substance and at least one of either an organic preservative acid or salt thereof, said UV-active indicator comprising a mixture of (a) either cationic pyrazoline or anionic stilbene and (b) either caffeine or quinine, said preservative in the form of an aqueous solution.

12. A detectable wood preservative comprising a UV-active indicator substance and at least one of either an organic preservative acid or a salt thereof, said organic preservative acid present in said wood preservative in amounts ranging from about 15.0 to 55.0% by weight, said wood preservative exhibiting shelf stability for up to 6 months.

* * * * *